United States Patent [19]

Wajaroff

[11] Patent Number: 4,470,423
[45] Date of Patent: Sep. 11, 1984

[54] PROCESS FOR PERMANENTLY SHAPING HAIR

[75] Inventor: Theodor Wajaroff, Darmstadt, Fed. Rep. of Germany

[73] Assignee: Wella Aktiengesellschaft, Darmstadt, Fed. Rep. of Germany

[21] Appl. No.: 453,883

[22] PCT Filed: May 4, 1982

[86] PCT No.: PCT/EP82/00092
§ 371 Date: Dec. 13, 1982
§ 102(e) Date: Dec. 13, 1982

[87] PCT Pub. No.: WO82/03985
PCT Pub. Date: Nov. 25, 1982

[30] Foreign Application Priority Data

May 16, 1981 [DE] Fed. Rep. of Germany ....... 3119634

[51] Int. Cl.$^3$ .............................................. A45D 7/04
[52] U.S. Cl. ............................................ 132/7; 424/70
[58] Field of Search ......................... 132/7; 424/70–71

[56] References Cited

U.S. PATENT DOCUMENTS

| | | | |
|---|---|---|---|
| 3,628,544 | 12/1971 | Kalopissis | 132/7 |
| 3,768,490 | 10/1973 | Kalopissis | 132/7 |
| 3,880,174 | 4/1975 | Wajaroff | 132/7 |
| 3,885,577 | 5/1975 | Edelberg | 132/7 |

Primary Examiner—Gregory E. McNeill
Attorney, Agent, or Firm—Michael J. Striker

[57] ABSTRACT

Multistage process for permanent shaping of hair, whereby the hair is at first treated with a liquid hair keratine reducing permanent shaping agent before and/or after rolling the hair onto rollers. This liquid, weak shaping effective permanent shaping medium is able to shape the hair in the area of the hair tips without damaging the hair tips during the reaction time. Subsequently, a consistent keratine reducing permanent shaping medium is applied to the rolled up hair which has a viscosity of 50 to 5000 m Pa·s, preferably 100 to 500 m Pa·s at a temperature of 30° C. and which has a stronger shaping effectiveness with respect to the liquid permanent shaping medium. The consistent permanent shaping medium screens the hair to the outside and prevents the access of atmospheric oxygen, on the one hand, and the escaping of a volatile alkalization agent like, for example, ammonia, on the other hand. Furthermore, due to the higher shaping effectiveness of the consistent permanent shaping medium a good shaping of the beginning of the hair is obtained without the danger of an excess curling of the tips of the hair. After a sufficient reaction time, the hair is rinsed and is then treated with an oxidating effective solution.

9 Claims, No Drawings

PROCESS FOR PERMANENTLY SHAPING HAIR

BACKGROUND OF THE INVENTION

In the common hair shaping processes the hair is at first treated with the watery solution of a reducing compound, in particular a mercapto compound, above all with thioglycolate in an alkaline medium or with a sulfite, preferably in a weak acid to neutral medium. Thereby, the disulfide bridge compounds of the hair keratine are split due to chemical separation and the hair is accessible to a permanent shaping.

The practical operation of the permanent shaping of human hair is generally performed in accordance with two variations. In accordance with one variation, the washed and towel dry hair is at first parted into a plurality of sections, thereafter these sections are pre-wetted with a portion of a liquid permanent shaping medium and finally the hair is then rolled onto rollers. After finishing the roller operation, the rollers are then afterwetted with the remainder of the liquid permanent shaping medium. In the other variation, the hair is also parted into a plurality of sections, after a preceeding hair washing and thereafter the hair is rolled on rollers without prewetting with a permanent shaping medium. After finishing rolling the hair onto the rollers, the rollers are thoroughly wetted with the total required quantity of the permanent shaping medium. The rollers being used for a permanent curling have a diameter of about 5 to 13 millimeter, while for a decurling rollers are required which have a diameter above 13 millimeter.

The reaction time of the hair shaping medium on the hair during the permanent curling as well as the permanent decurling takes up to about 30 minutes depending on the condition of the hair and the desired degree of shaping. The reaction time can be shortened by means of a heat supply, for example, by using a heat radiator or a hair drier.

After the duration of the required reaction time of the hair shaping medium the rolled up hair is rinsed with water and is fixed into the new shape with the watery solution of an oxidation medium, preferably with a 2% hydrogen peroxide solution, while again reestablishing the previously split disulfide compounds of the hair keratine.

Thereby, the reaction time of the fixing medium is generally 10 to 15 minutes. Finally, the rollers are removed and the hair is thoroughly rinsed with water. During the reaction time of the hair shaping medium and in particular when supplying heat, a large part of the ammonia, present as an alkalisation medium in the preparations, escapes. Furthermore, portions of the mercapto compound or the sulfite, contained as reductive acting permanent shaping ingredients, are oxidized by the atmospheric oxygen, due to the large surface of the hair. It the hair-shaping medium is acid adjusted, a decomposition of the wave shaping ingredient can occur with a separation of foul smelling hydrogen sulfide. The missing screening for the rollers finally results in a loss of liquid and heat. Naturally, the mentioned effects are stronger on the outer layers of the rolled up hair, that is, in the area of the hair close to the head than in the inner layers of the hair. Consequently, the permanent shaping in the area of the hair in close proximity to the head is unsatisfactory. If, in contrast thereto, one would prolong the reaction time or select a stronger, more effective shaping medium, one would obtain a sufficient shaping of the hair in the proximity to the head; however the tips of the hair would be damaged.

This negative result is also increased because the tips of the hair are more sensitive to chemical reactions than the hair in the proximity of the head. In addition, the tips of the hair are at first rolled onto the roller and are therefore curled more strongly than the beginning of the hair at the proximity of the head, which is superimposed on tips of the hair.

However, it is the aim of a permanent hair shaping to obtain a uniform shaping of the hair, from the tips of the hair to the beginning of the hair, without damaging the tips of the hair.

A screening of the rollers can be obtained by using a foam like permanent shaping medium. Thereby, a closed stable foam layer is applied onto the rollers. However, thereby the unavoidable simultaneous wetting of the scalp as well as the uncontrollable running off of the shaping liquid from the decomposing foam is disadvantageous.

With the screening of the rollers recommended in the German laid open patent No. 2,822,125 by means of a layer of a finely granulated solid material or by covering the hair with a plastic cover, a certain success with respect to screening is obtained, however the different sensitivity of the hair between the beginning of the hair and the tips of the hair with respect to a chemical shaping is thereby not equalized.

SUMMARY OF THE INVENTION

It is therefore an object of the invention to provide a method for a permanent shaping of hair, wherein the aforementioned disadvantages are avoided and with which a reliable and uniform shaping of the hair is obtained in a simple manner.

It was now found that the object of the invention is obtained in an excellent manner by a process for a permanent shaping of hair which is characterized in that
 (a) the hair is treated with a liquid hair keratine reducing permanent shaping medium before rolling it on rollers and/or after the rolling on rollers,
 (b) subsequently applying onto the rolled hair a consistent hair keratine reducing permanent shaping medium with a viscosity of 50 to 5000 m Pa·s/at 30° C. and a stronger shaping effectiveness with respect to the liquid permanent shaping medium,
after a sufficient reaction time the permanent shaping medium mixture is rinsed off the hair and the hair is treated with an oxidizing effective solution.

The liquid permanent shaping medium as well as the consistent permanent shaping medium which is to be used in the inventive process contain as a shaping effective hair keratine reducing active material sulfite or defined mercapto compounds, in particular salts or derivatives of the thioglycolic acid, like ammonium thioglycolate, ammonium thiolactate and glycerine monothioglycolate. However, it is not required that the liquid and the consistent permanent shaping medium contain the same hair keratine reducing active material.

As a liquid permanent shaping medium any weak shaping effective liquid permanent shaping medium for the hair is to be considered which during the general reaction time of about 10 to 30 minutes is able to shape the hair in the area of the hair tips, however whose shaping effectiveness is too low for damaging the hair tips in this period of time. Suitable liquid permanent shaping media are, for example, such with a content of about 4 to 10 weight % ammonia thioglycolate and a pH value of about 7-8. Further suitable liquid permanent shaping media can be taken from the following examples.

The consistent permanent shaping medium in the described process has a viscosity of 50-5000 m Pa·s (millipascal seconds) at a temperature of 30° C. and has a higher shaping effectiveness than the liquid permanent shaping medium previously applied to hair.

Since the shaping effectiveness of a permanent shaping medium does not alone depend from the concentration of the hair keratine reducing active material and the adjusted alkalinity, but further contained materials, like for example, defined hair caring additives have an influence on the shaping effectiveness, it is safely determined by comparing experiments. The permanent shaping medium which is the more shaping effective is the one which performs the same shaping in the shorter time under the same application conditions, that is, by using the same rollers, same temperature and the same pull during rolling on the same hair.

For example, the consistent permanent shaping medium can be more shape effective than the liquid permanent shaping medium based on the following factors:
higher concentration of the hair keratine reducing active material
stronger effectiveness of the hair keratine reducing active material
higher content of the alkalization medium (high pH value).

Naturally, a higher shape effectiveness can also be the result of a combination of the aforementioned factors.

Incidentally, the consistent permanent shaping medium represents a dispersion, an emulsion or a mixture of a watery solution of a known hair keratine reducing active material and, if need be, an alkalization medium with suitable filler materials, thickeners and/or emulsifiers, as well as the usual additives in a hair shaping medium which is adjusted by a suitable selection of the type and quantity of the contained filler materials, thickeners and/or emulsifiers to a viscosity of 50 to 5000 m Pa·s, preferably 100 to 500 m Pa·s at 30° C. In particular, it is present in the form of a gel or a cream.

For example, kaolin, montmorillonite and/or calcium carbonate are considered as suitable filler materials, while as thickeners one can use, for example, wheat flour, tylose, starch, gelatine, cellulose derivatives and carboxy vinyl polymerisates. As compounds which result in a stable cream in conjunction with a suitable emulsifier, higher fatty alcohols, fatty acid esters, liquid and solid paraffines, ispraffines, vaseline and wool wax may be mentioned. Suitable emulsifiers are, among others, fatty alcohol sulfides, fatty acid alkanolamide, alkylsulfonate, alkyl benzol sulfonates, and oxethylated nonylphenols. Furthermore, the liquid as well as the consistent permanent shaping medium may contain additives customary in cosmetic preparations, for example, antioxidents, perfume oils, complex formers, dyes, low aliphatic alcohols, like ethanol and isopropanol, wetting agents, turbidity agents, protective and caring additives, like urea, lanolin derivatives, cholesterin and pathothenic acid.

In the inventive process, the washed and towel dried hair is either immediately saturated (prewetted) with the liquid, weaker shaping effective permant shaping medium, or the hair is at first separated into sections, rolled onto rollers and then saturated with the liquid permanent shaping medium. It is also possible to saturate the hair before and after the rolling up process with the liquid permanent shaping medium (pre-and afterwetting), for a more intensive penetration. In order to protect the hands of the beautician, it is preferred to use the method, whereby the hair is wetted with the liquid permanent shaping medium, after the hair is rolled on the rollers. Thereby, the hands of the beautician do not come into contact with the shaping shaping medium. The consistent, stronger permanent effective permanent shaping medium is now applied in a closed layer onto the wetted hair which is rolled on the rollers and saturated with the liquid permanent shaping agent. For application purposes, the consistent permanent shaping medium can be applied directly to the hair from a tube or a pressure gas package, or it can be applied with an auxiliary means, like a brush or a spatula.

After a sufficient reaction time, which is about 10 to 30 minutes, depending on the condition of the hair, temperature (the application temperature is about 25 to 50° C.) and the desired degree of shaping, the rolled up hair is thoroughly rinsed with water and is then fixed in the new shape by treating the hair with the watery solution of an oxidation medium.

With respect to the known processes, the novel inventive process for the permanent shaping of hair has numerous advantages.

The hands of the beautician, if he applies the method of the prewetting (before rolling up the hair), come into engagement only with a weak shaping effective and therefore less aggressive liquid permanent shaping medium. Furthermore, only the liquid, weak shaping effective permanent shaping medium is effective on the sensitive hair tips, since the later applied consistent, stronger shaping effective permanent shaping medium cannot penetrate into the innermost layers of the rolled up hair. Finally, a screening is obtained for the rollers by means of the consistent permanent shaping medium. This screeing substantially eliminates the access of atmospheric oxygen and simultaneously reduces the escaping of volatile alkalization medium, like ammonia, as well as the drying out of the uppermost layer of the rolled up hair considerably.

The screening effect of the consistent permanent shaping medium can be demonstrated in conjunction with the following experiments:

Two strands of hair of uniform weight and of the same hair are rolled onto rollers with the same diameter and are wetted with the same quantity of a permanent shaping liquid. Subsequently, an inventive consistent permanent shaping medium in accordance with example 3 is applied to one of the rollers.

If one uses as a permanent shaping liquid, a watery solution containing 8% by weight cystein as the reduction medium, the loss of the reduction medium within one hour without using a screen is about 45%, while with the use of a screen it is only about 7%.

If one places a bubble cap over a roller which is saturated with a weak acid adjusted permanent shaping medium on the basis of monothioglycolic acid glycerine ester and if one places a lead acetate paper below the bubble cap, the lead acetate paper is colored black due to the hydrogen sulfide which escapes from the roller because of decomposition. However, if the roller is covered with an inventive consistent permanent shaping medium, the test reaction for hydrogen sulfide fails.

Finally, due to the exclusive active reaction of the stronger shaping effective consistent permanent shaping medium on the beginning of the hair in the proximity of the scalp, a desired good shaping is obtained also in this critical area.

The inventive process is suited very well for the permanent curling of hair, as well as for decurling the hair. Thereby, only the diameter of the rollers of 5 to 13 millimeters for permanent curling and of over 13 millimeters for the decurling must be adjusted, corresponding to the kind of application.

The novel features which are considered as characteristic for the invention are set forth in particular in the appended claims. The invention itself, however, both as to its construction and its method of operation, together with additional objects and advantages thereof, will be best understood from the following description of specific embodiments.

DESCRIPTION OF THE PREFERRED EMBODIMENTS

Example 1 Process for permanent curling of hair

The washed and towel dried hair is uniformly prewetted with 20 g of a liquid permanent shaping medium A1 having the composition:

(A1) Liquid permanent shaping medium

| | |
|---|---|
| 6,0 g | ammonium thioglycolate, 50% watery solution |
| 1,5 g | ammonium hydrogen carbonate |
| 0,2 g | 1,4-nonylphenol, with 10 Mol ethylene oxide oxethylated |
| 0,1 g | perfume oil |
| 42,2 g | water |
| 50,0 g | | having a pH-value of 7,8 and a viscosity of 1 m Pa·s at 30° C. and is subsequently rolled onto permanent wave rollers. Thereafter, the rolled hair is carefully afterwetted with the remainder quantity of 30 g of the permanent shaping medium A1.

Now, on the rolled up hair the total quantity of 50 g of a consistent and in comparison to A1 more strongly shaping effective permanent shaping medium B1 or C1 is applied with the aid of a brush in a uniform layer having the composition:

(B1) Consistent permanent shaping medium

| | |
|---|---|
| 12,0 g | ammonium thioglycolate, 50% watery solution |
| 1,0 g | ammonium hydrogen carbonate |
| 2,0 g | ammonium carbonate |
| 1,0 g | glycerine monostearate |
| 3,0 g | cetylalcohol |
| 0,4 g | oleylalcohol with 10 Mol ethylene oxide oxethylated |
| 0,3 g | 2-Octyldodecanol |
| 0,2 g | paraffine oil |
| 0,1 g | perfume oil |
| 30,0 g | water |
| 50,0 g | |

(This emulsion has a pH-value of 8,7 and a viscosity of 300 m Pa·s at 30° C.)

(C1) Consistent permanent shaping medium

| | |
|---|---|
| 12,0 g | ammonium thioglycolate, 50% watery solution |
| 1,0 g | ammonium hydrogen carbonate |
| 2,0 g | ammonium carbonate |
| 0,8 g | stearyl alcohol |
| 0,4 g | cetyl alcohol |
| 0,1 g | cetyl alcohol with 10 Mol ethylene oxide oxethylated |
| 0,1 g | cetyl trimethyl ammonium chloride |
| 0,1 g | perfume oil |
| 33,5 g | water |
| 50,0 g | |

(This emulsion has a pH-value of 8,8 and a viscosity of 50 m Pa·s at 30° C.)

After a reaction time of the consistent permanent shaping medium of 20 minutes, the hair is thoroughly rinsed with warm water, the surplus dampness is removed with a paper napkin and subsequently the hair is treated with a 2% watery hydrogen peroxide solution for fixing.

Example 2 Process for permanent curling of hair

The washed and towel dried hair is rolled up on permanent wave rollers and subsequently thoroughly wetted with the total quantity of 50 g of a liquid permanent shaping medium A2 having the composition:

(A2) liquid permanent shaping medium

| | |
|---|---|
| 4,0 g | monothioglycol acid glycerin ester |
| 46,0 g | water |
| 50,0 g | | and a pH-value of 6,5 and a viscosity of 0,8 m Pa·s at 30° C. Thereafter, a more consistent and more stronger shaping effective permanent shaping medium B2 or C2, that is stronger with respect to A2, is applied to the hair with a brush with a composition as follows:

(B2) consistent permanent shaping medium

| | |
|---|---|
| 9,5 g | ammonium thioglycolate, 50% watery solution |
| 1,5 g | ammonium hydrogen carbonate |
| 1,5 g | ammonium carbonate |
| 0,7 g | ammonia, 25% watery solution |
| 0,3 g | 1,4-nonylphenol with 10 Mol ethylene oxide oxethylated |
| 1,3 g | carbonyvinyl polymerisate (CARBOPOL 934 ® from company B. F. Goodrich, Cleveland/Ohio, USA) |
| 0,2 g | perfume oil |
| 35,0 g | water |
| 50,0 g | |

(This permanent shaping medium as a gel has a pH-value of 8,8 and a viscosity of 3600 m Pa·s at 30° C.)

(C2) consistent permanent shaping medium

| | |
|---|---|
| 16,0 g | watery, 33% ammonium sulfite solution |
| 10,0 g | imidazolidinon-2 |
| 0,8 g | tylose |
| 2,8 g | isopropanol |
| 0,2 g | perfume oil |
| 20,2 g | water |
| 50,0 g | |

(This permanent shaping medium in form of a gel has a pH-value of 6,5 and a viscosity of 1900 m Pa·s at 30° C.)

One covers the hair with a plastic cover and applies heat with a hair drier.

After a reaction time of 10 minutes beneath the hair drier, the plastic cover is removed and the hair is thoroughly rinsed with lukewarm water and the superfluous water is removed by means of a paper napkin. Finally, the hair is treated with a 10% watery solution of sodium bromide for fixing the hair.

Example 3 Process for the permanent decurling of hair

Curled hair is prewetted with 20 g of a liquid permanent shaping medium A3 with the composition:

(A3) liquid permanent shaping medium

| | |
|---|---|
| 6,2 g | ammonium thiolactate, 50% watery solution |
| 1,2 g | ammonia, 25% watery solution |
| 0,4 g | oleic acid pentaerythrit polycol ether |
| 0,4 g | perfume oil |
| 41,8 g | water |
| 50,0 g | | which has a pH-value of 9,8 and a viscosity of 1 m Pa·s at 30° C. and the hair is subsequently rolled onto a roller with a diameter of 24 millimeter. Thereafter, the rolled up hair is afterwetted with the remainder quantity of 30 g of the liquid permanent medium A3.

Now, the total quantity of 50 g of a consistent and in comparison with A3 stronger shaping effective permanent shaping medium B3 is applied to the rolled up hair with a composition of:

(B3) consistent permanent shaping medium

| | |
|---|---|
| 10,0 g | ammonium thioglycolate, 50% watery solution |
| 2,0 g | ammonia, 25% watery solution |
| 3,0 g | cetyl stearyl alcohol |
| 0,5 g | sodium lauryl sulfate |
| 0,5 g | perfume oil |
| 34,0 g | water |
| 50,0 g | | which is present in form of an emulsion with a pH-value of 9,6 and a viscosity of 105 m Pa·s/at 30° C. With the aid of a brush, it is applied in a uniform layer. After a reaction time of 15 minutes, the hair is thoroughly rinsed with lukewarm water and the superfluous water is removed by dabbing with a towel. Thereafter, the hair is treated with a 2,5% watery hydrogen peroxide solution for about 15 minutes for fixing the hair. Finally, the oxidation medium is removed by a thorough rinsing of the hair with water and the hair is dried on the rollers.

All aforementioned percentage statements represent percentages by weight.

I claim:

1. Process for the permanent shaping of hair, comprising
    (a) treating the hair with a liquid, hair keratine-reducing, permanent shaping medium before or after rolling it on rollers;
    (b) subsequently applying onto the rolled hair a consistent, hair keratine-reducing, permanent shaping medium with a viscosity of 50 to 5000 m Pa·s/at 30° C. and a stronger shaping effectiveness compared to that of the liquid permanent shaping medium, after a sufficient reaction time, rinsing the permanent shaping medium mixture off the hair and treating the hair with an oxidizing effective solution.

2. Process in accordance with claim 1, wherein the liquid and the consistent permanent shaping medium each contain one mercapto compound as the hair keratine-reducing active material.

3. Process in accordance with claim 1, wherein the consistent hair keratine-reducing permanent shaping medium has a viscosity of 100 to 500 m Pa·s at a temperature of 30° C.

4. Process in accordance with claim 1, wherein the consistant permanent shaping medium is present in the form of a gel or a cream.

5. Process in accordance with claim 1, wherein the reaction time of the consistent permanent shaping medium on the hair is about 10 to 30 minutes at a temperature of 25° C. to 50° C.

6. Process in accordance with claim 1, wherein the liquid permanent shaping medium has a weaker shaping effectiveness than the consistent permanent shaping medium, which is sufficient to shape the hair in the area of the hair tips, but which is not sufficient to damage the hair tips during a reaction time of 10 to 30 minutes.

7. Process in accordance with claim 1, wherein the liquid permanent shaping medium contains about 4 to 10% by weight ammonium thioglycolate and has a pH-value of about 7 to 8.

8. Process in accordance with claim 1, wherein that process is a process for the permanent curling of hair.

9. Process in accordance with claim 2, wherein the mercapto compound is a salt or an ester of thioglycolic acid.

* * * * *